United States Patent [19]

Callahan

[11] 4,353,253

[45] Oct. 12, 1982

[54] DEVICE FOR MEASURING THE DENSITY OF FLUIDS

[76] Inventor: George E. Callahan, Feldstrasse 34, 4000 Dusseldorf 30, Fed. Rep. of Germany

[21] Appl. No.: 145,890

[22] Filed: May 2, 1980

[51] Int. Cl.$^3$ .......................... G01N 9/16; G01N 9/20
[52] U.S. Cl. ....................................... 73/454; 73/440; 73/322.5
[58] Field of Search ................. 73/454, 440, 441, 448, 73/449, 451

[56] References Cited

U.S. PATENT DOCUMENTS

| | | | |
|---|---|---|---|
| 2,296,169 | 9/1942 | Linebarger | 73/454 |
| 2,409,310 | 10/1946 | Piper | 73/65 |
| 2,579,220 | 12/1951 | Vine | 73/65 X |
| 2,674,119 | 4/1954 | Trainor | 73/454 |
| 2,674,120 | 4/1954 | Trainor | 73/454 |
| 3,691,847 | 9/1972 | Wallskog | 73/454 X |
| 3,908,467 | 9/1975 | Schwen et al. | 73/454 |
| 4,037,481 | 7/1977 | Callahan | 73/454 |
| 4,136,551 | 1/1979 | Lunstroth | 73/32 R |
| 4,236,405 | 12/1980 | Lunstroth | 73/32 R |

Primary Examiner—Daniel M. Yasich
Attorney, Agent, or Firm—William R. Hinds

[57] ABSTRACT

A device for measuring the density of fluids comprises two float elements of unequal density distribution pivotally mounted on a common axis about which they rotate in opposite directions with change of density of the fluid in which they are immersed. The density is indicated by the position of an index carried by one element relative to a scale carried by the other element. Scale range is increased and scale linearity is improved by having the elements respond respectively differently to density changes in the upper and lower density ranges. Temperature compensation is effected by the choice of materials for the float elements relative to the thermal expansion characteristics of the fluid, and by the manner in which the relatively more dense and relatively less dense portions of each float element are mounted with respect to the axis. The float elements may be mounted in an at least partially transparent housing into which the fluid may be drawn through an expanding channel formed as an inverted U-tube in which separated bubbles collect.

11 Claims, 22 Drawing Figures

DEVICE FOR MEASURING THE DENSITY OF FLUIDS

FIELD OF THE INVENTION

The present invention relates to devices for measuring the density of fluids by means of pivotally mounted, weighted floats. It is generally concerned with means of modifying the linearity of the measuring scale while simultaneously expanding the scale in order to permit more accurate readings. It is further and particularly concerned with improving the temperature-error correction, so that accurate readings may be made over a wide range of temperatures. Finally, it is concerned with reducing the risk of erroneous readings caused by the added bouyancy of incidental air bubbles, which in practice often falsify measurements made wth such devices.

It will be understood that the measuring scale of such a device may be calibrated to read in other units (e.g., units expressing concentration, where the density of a solution varies with its concentration), but since this is merely a design expedient, all references hereinafter will be to fluid density, which is what such devices actually respond to.

DESCRIPTION OF THE DRAWINGS

In order that the invention may be clearly understood and readily carried into effect, examples of fluid density measuring devices in accordance therewith and their relationship to the prior art, so far as that is known, will now be described with reference to the accompanying drawings, in which:

FIG. 1 shows an alternative to FIG. 9;

DESCRIPTION OF PREFERRED EMBODIMENTS

The use of pivotally mounted, weighted floats for measuring fluid density is well known, as shown, for instance, in U.S. Pat. Nos. 4,136,551 and 3,908,467, and in my earlier U.S. Pat. No. 4,037,481. However, such devices generally are not discussed in textbooks, and since an understanding of their principle of operation may be required by the specification hereinafter, it is briefly described below with reference to FIG. 1.

Figure 1:
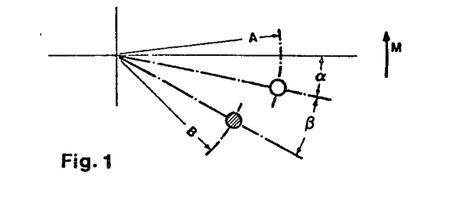
FIG. 1 is a diagram of a weighted float.

Such a density-responsive float element consists of a pivotally mounted bouyant element combined with a weight element in such a manner that the following criteria are fulfilled over the entire measuring range: 1. The radial line connecting the pivot with the center of bouyancy has a higher angle (more positive) with reference to the horizontal than the radial line connecting the pivot with the center of gravity, i.e., the float element is hydrostatically stable; 2. The density of the fluid (which the float element is to measure) is greater than the density of the bouyant element, and less than the density of the weight element, i.e., if the fluid density is $\rho$, the density of the buoyant element $\rho_a$, and the density of the weight element $\rho_b$, then the inequality $\rho_a < \rho < \rho_b$ is valid for all values of $\rho$.

The geometry of such a float element is shown in FIG. 1, where the radial line connecting the pivot with the center of bouyancy is displaced from the horizontal by an angle $\alpha$, and separated from the radial line connecting the pivot with the center of gravity by an angle $\beta$. If the volume of the bouyant element is $V_a$ and its center of bouyancy is at a radial distance A from the pivot, and the volume of the weight element is $V_b$ and its center of gravity is at a radial distance B from the pivot, the torque resulting from the couple of bouyant and gravitational force is:

$$M = \rho\{V_a A \cos\alpha + V_b B \cos(\alpha-\beta)\} - \rho_a V_a A \cos\alpha - \rho_b V_b B \cos(\alpha-\beta) \quad \text{Equation (1)}$$

When immersed in a fluid, such an element will assume an angle at which torque is zero. The greater the relative density of the fluid, the higher (more positive) angle $\alpha$ will be. This is a stable condition which is expressed by:

$$(\rho - \rho_a)V_a A \cos\alpha = (\rho_b - \rho)V_b B \cos(\alpha-\beta) \quad (2)$$

The angle which such an element will assume in a fluid of a given density may be taken from a rearrangement of (2), in which the first term describes the geometry of the float, the second term the relation of the densities, and the third term the corresponding angles:

$$\frac{V_b B}{V_a A} \cdot \frac{\rho_b - \rho}{\rho - \rho_a} = \frac{\cos\alpha}{\cos(\alpha - \beta)} \quad (3)$$

The above expressions for length, volume, and density are assumed to be valid at some standard temperature. When subsequently considering the effects upon density measurements made at temperatures which differ from that standard temperature, it is obvious that all will be affected by thermal expansion. When dealing with materials in which the coefficient of thermal expansion may vary with temperature, thermal expansion can be expressed by the dimensionless relation between a length L at the standard temperature and the change in this length $\Delta L$ at a different temperature $\theta$. Thus, at temperature $\theta$, any standard-temperature length $L$ will be changed by the factor $$1 + \frac{\Delta L}{L},$$

and this changed length will be $$L_\theta = L\left(1 + \frac{\Delta L}{L}\right).$$

Since $\Delta L$ is small, the resulting change in volume can be taken to be $3\Delta L$, so that the standard-temperature volume $V$ will be changed to $$V_\theta = V\left(1 + 3\frac{\Delta L}{L}\right).$$

This volume change obviously results in an inverse density change, so that $$\rho_\theta = \frac{\rho}{1 + 3\frac{\Delta L}{L}}.$$

If the thermal expansion $\Delta L/L$ of the buoyant element is written simply $\Delta a/a$, and the thermal expansion of the weight element $\Delta b/b$, and the preceding expressions describing changes in length, volume, and density are introduced into equation (1), the angle which a float element will assume in a fluid of density $\rho_\theta$ at temperature $\theta$ may be taken from:

$$\frac{V_b B}{V_a A} \cdot \frac{\rho_b - \rho_\theta\left(1 + 3\frac{\Delta b}{b}\right)}{\rho_\theta\left(1 + 3\frac{\Delta a}{a}\right) - \rho_a} = \frac{\cos\alpha}{\cos(\alpha - \beta)} \quad (4)$$

This equation is analogous to (3), and the fact that the first terms of each are identical is typical of float elements where, in agreement with previous practice, the weight element is structurally incorporated into the bouyant element. In this case, the thermal expansion of the bouyant material governs the change of both lengths A and B, so that these are proportional and therefore without effect on the thermal expansion characteristics of the float.

Since one of the purposes of the present invention is to provide improved temperature-error correction, structural means of influencing the thermal expansion characteristics of a float element will be proposed later. This requires the concept of an "attachment radius", which is the distance from the pivotal point of the float to the fixed attachment point of the buoyant element $R_a$ and the corresponding distance for the weight element $R_b$. The introduction of these terms avoids the restriction stated for (4), so that thermal expansion effects in any type of float are described by:

$$\frac{V_b B\left(1 + \frac{\Delta b}{b} + \frac{R_b}{B}\left(\frac{\Delta a}{a} - \frac{\Delta b}{b}\right)\right)}{V_a A\left(1 + \frac{\Delta a}{a} + \frac{R_a}{A}\left(\frac{\Delta b}{b} - \frac{\Delta a}{a}\right)\right)} \cdot \quad \text{Equation (5)}$$

$$\frac{\rho_b - \rho_\theta\left(1 + 3\frac{\Delta b}{b}\right)}{\rho_\theta\left(1 + 3\frac{\Delta a}{a}\right) - \rho_a} = \frac{\cos\alpha}{\cos(\alpha - \beta)}$$

Figure 2:
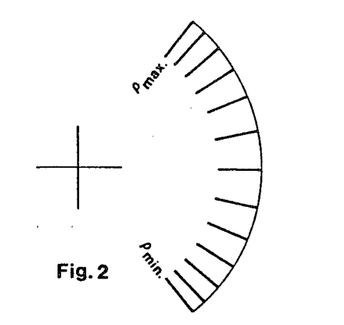
FIG. 2 shows a scale associated with the device of FIG. 1.

Equation (3) may be applied to any typical float element at standard temperature for deriving the changes in float angle $\alpha$ corresponding to equal increments of fluid density; the result will be as shown in FIG. 2. It will be seen that equal increments of density correspond to very unequal increments of float angle, and that this non-linearity limits the practically usable angular range of about 80° or less. This is an unavoidable characteristic of such devices, so that acceptable linearity in the measuring scale can be achieved only by restricting the total scale angle, i.e., by reducing either the measuring range, or the distance between scale subdivisions, or both.

Figure 3:
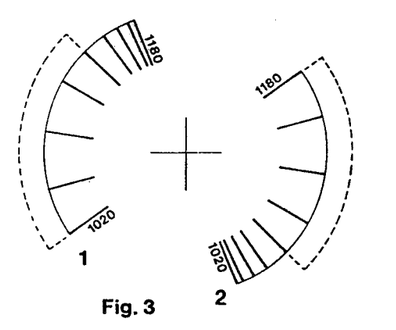
FIG. 3 shows an example of individual float angles corresponding to equal increments of fluid density.

As an example of a feature incorporated in the present invention, FIG. 3 shows angular scales 1 and 2 corresponding to equal increments of fluid densities between 1020 and 1180 kg/m$^3$ for a pair of float elements. Scale 1 applies to a float element 1 which has obviously been designed to respond with relatively large angular increments in the lower part of this density range, whereas scale 2 applies to a float element 2 which has been designed contrarily. Since the sector of greater angular increments is the sector of greatest measuring accuracy, it may be said that float 1 responds predominantly in the lower part of the density range, and float 2 in the upper part. As such, each float element may be considered as comprising means for responding to equal increments of fluid density within the predetermined range with relatively larger angular increments of rotation in its assigned part of the predetermined range. If each float is thus considered to predominate in half of the total range, it will be seen that each half-range encompasses an angle of 80°, shown by dashed lines, wherein the angular increments are not equal (it has been said that this is impossible to achieve), but are relatively widely spaced. According to preferred embodiments of the present invention, one of these float elements is to carry a scale, and the other is to carry an index which can be read against the scale. This concept is known per se from U.S. Pat. No. 4,136,551.

Figure 4:
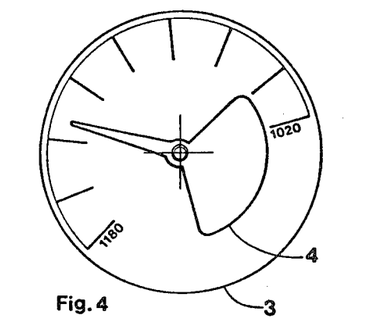
FIG. 4 shows an embodiment of float elements and a resulting density scale.

FIG. 4 shows an embodiment corresponding to 1 of FIG. 3, in the form of scale element 3, and an embodiment corresponding to 2 of FIG. 3, in the form of index element 4. The two elements are free to rotate around a common axis. Scale element 3 carries a scale of angular increments corresponding to the relative angular displacement of the two elements at the specified densities, which can be confirmed as being the sums of the angular increments of the individual elements as shown in FIG. 3. From FIG. 4 it is apparent that the linearity of the resulting scale is comparatively excellent (being much better than that of the 80° half-ranges of FIG. 3), and that, moreover, the scale has been expanded to encompass 210° (which is 30% more than the combined 80° half-ranges of FIG. 3). The combination of float elements is therefore markedly superior to a simple "addition" of floats and associated scales, in regard to both scale linearity and total scale angle.

It will be noted that the scale of FIG. 4 is symmetrical around the mid-point, and it may be correctly inferred that this is a consequence of the inverse symmetry of scales 1 and 2 of FIG. 3. Obviously the scale angles shown in FIG. 3 are in no way mandatory—by assigning a different angular range to the given density range, different angular increments would result—nor need the scales be symmetrical in any way. A salient advantage is to be seen in the fact that the angles assigned to each float element can be varied at will, e.g., to expand or contract the resulting scale either as a whole or at any desired point, symmetrically or asymmetrically.

Figure 5:
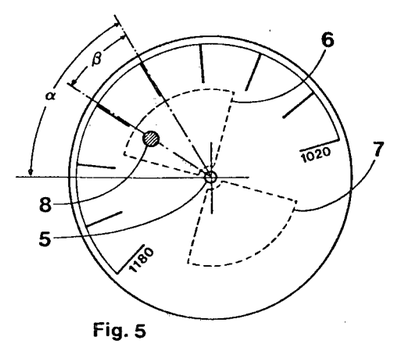
FIGS. 5 and 6 show the embodiment of FIG. 4 in greater detail.

FIG. 5 shows the embodiment of scale element 3 of FIG. 4 in greater detail. If this element were a circular plate of uniform thickness, it would be hydrostatically neutral around the centrally located pivot 5. If it is made of bouyant material a hydrostatically effective bouyant volume ($V_a$) can be achieved by increasing the thickness of the plate e.g., within the area 6. Angle $\alpha$ must then be taken from the radial line connecting the pivot with the center of bouyancy of the added volume. Alternatively to increasing the plate thickness within area 6, the plate thickness can be reduced—or the plate material completely omitted—within the area 7, diametrically opposed to area 6, whereby the same effect is achieved. A hydrostatically effective bouyant volume can also be achieved by omitting some sector of the plate entirely, or by locating the pivot 5 off-center of the circular plate of uniform thickness. In this example, a weight element 8 is structurally incorporated into the bouyant element, as is common practice.

Figure 6:
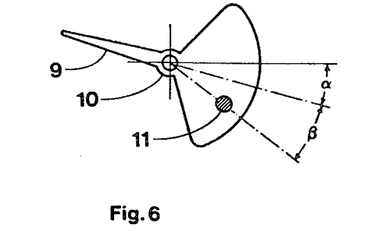

FIG. 6 shows the embodiment of index element 4 of FIG. 4 in greater detail. The index element can of course be constructed according to the principles already described with reference to the scale element (e.g., by using a circular plate of smaller diameter, so that the scale is not obscured from view). However, any volume which is not symmetrical about the pivotal point will be hydrostatically effective, so that it may be preferable to construct the index element as shown, whereby the bouyant element is a circular sector fitted with an index 9. It will be noted that the index 9 may be angularly displaced with reference to angle $\alpha$, for instance to increase scale readability, but that of course the associated scale must be similarly displaced with reference to angle $\alpha$ of scale element 3. In this example, the pivotal connection has the form of a ring 10 which can rotate about the pivot 5 of scale element 3, so that both elements pivot about a common axis. A weight element 11 is structurally incorporated into the bouyant element, as is common practice.

In FIGS. 4, 5 and 6 the two elements are so designed that the index element is positioned in front of the scale element. This order can naturally be reversed by positioning the scale element in front, as long as some index point remains visible, so that it can be read against the scale. It should also be noted that whereas scale element 3 is associated with the angular scale 1 of FIG. 3, and index element 4 is associated with the angular scale 2 of FIG. 3, this order is optional, and can be reversed without altering any of the principles involved or affecting any characteristics of the resulting density scale.

From the foregoing it is obvious that both float elements are free to assume angles to the horizontal in agreement with equation (3), whereby their relative angular position is an indication of the density of the fluid in which they are immersed. This is a further inherent advantage of this embodiment of the present invention, inasmuch as the density reading is completely independent of any type of "artificial horizon", as is mandatory in some previous devices of this type (an example of which is described in my U.S. Pat. No. 4,037,481).

Since devices of this type are often used for density measurements at varying temperatures, the "temperature error" of such devices is important. The temperature error in angular degrees for any float element of typical construction is the difference in the angles $\alpha$ as calculated from equation (3) and equation (4). in previous practice, metallic weight elements have been used, and because of their small volume (high density) and low coefficients of thermal expansion, their contribution to temperature error is negligible. In such cases, temperature error derives from the difference between the thermal expansion of the bouyant element and that of the fluid. Typical fluids (battery acids, anti-freeze solutions) have different coefficients of thermal expansion at different densities (the fact that these coefficients also vary with temperature will be discussed later), so that complete temperature compensation can be obtained for only a single fluid density. This would be the case when the thermal expansion of the bouyant element is identical with that of the fluid. Other densities of the same fluid, having other coefficients of thermal expansion, would still be subject to temperature error in all measurements not made at the standard temperature for which the device was designed. (For this reason, U.S. Pat. No. 3,908,467 proposes a plurality of float elements and associated scales, in order to reduce temperature error by reducing the density range assigned to each float element). Under the above assumptions, temperature compensation is reduced to the selection of a bouyant material with a thermal expansion corresponding most closely to an "average" thermal expansion of the fluid within the measuring range of the instrument.

Figure 7:
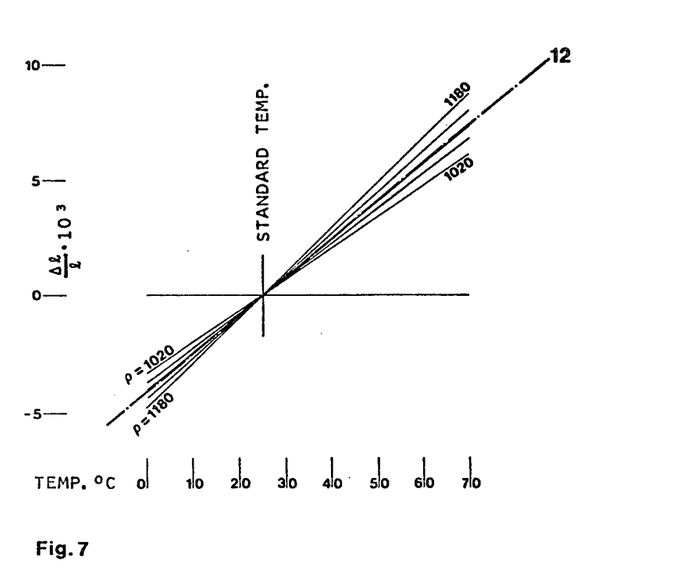
FIG. 7 shows idealized thermal expansion curves which are typical of those encountered in practice.

For a more ready understanding of thermal effects in devices of this type, the thermal expansion typical of the materials in question can, for the sake of simplicity, be assumed to be a linear function of temperature change. Under this assumption, the thermal expansion curves of an idealized fluid would appear as straight lines, as shown in FIG. 7, where the fluid density is assumed to vary from 1020 to 1180 kg/m$^3$, and where the coefficient of thermal expansion of the fluid typically increases with increasing density. Curve 12 would then represent the thermal expansion of a bouyant material best "averaging" the thermal expansion of the fluid, and therefore providing the best possible correction of temperature error.

Figure 8:
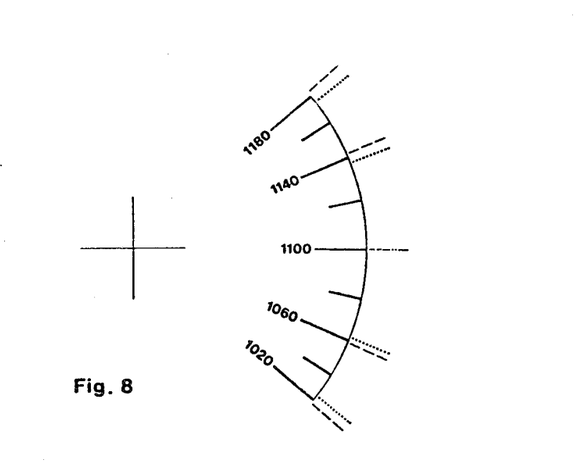
FIG. 8 shows the resultant temperature error in a device of known form.

FIG. 8 shows the resultant temperature error if the thermal expansion characteristics of FIG. 7 are applied to a float element which is typically assumed to have a total scale angle of 80° within the assumed density range. The scale calibration is for the standard temperature shown in FIG. 7, the temperature range is from 0° C. to +70° C. For selected densities, the temperature error at 0° C. is shown as a dashed line, and the corresponding temperature error at +70° C. is shown as a dotted line. Temperature error has been fully corrected at fluid density 1100 kg/m$^3$, inasmuch as here the thermal expansion of the bouyant material is identical with that of the fluid. Temperature errors are greatest at the extremes of the density range, and that the sign of this error is reversed from one extreme to the other is an obvious consequence of the relative thermal expansions shown in FIG. 7.

Here it should be pointed out that angular differences resulting from thermal expansion are not actually a satisfactory indication of temperature error, since this would be more significant if expressed in terms of indicated density. Obviously, where scale subdivisions are widely spaced, a given angular difference represents a much smaller difference of indicated density that if the scale subdivisions at that point were narrowly spaced. Thus it may be concluded from FIG. 8, that, although the angular errors at the extremes of the scale are not large, the errors of indicated density are in the order of +5 kg/m$^3$, and that this is to be taken as the maximum temperature error of the instrument.

The foregoing principles can be applied to the present invention with reference to the same idealized fluid, assuming the angles of the floats at standard temperature to be identical with those shown in FIG. 3. If again, float 1 of FIG. 3 is assumed to predominate in the lower part of the density range, i.e., from 1020 to 1100 kg/m$^3$, it would be analogous to the previous example to assume a bouyant material with a thermal expansion close to that of the fluid at density 1060 kg/m$^3$. Conversely, float 2 should have nearly the same thermal expansion as that of the fluid at a density of 1140 kg/m$^3$. This assumption is shown graphically in FIG. 9, where curves 13 and 14 represent the thermal expansion of the bouyant materials of floats 1 and 2 respectively.

Figure 10A:
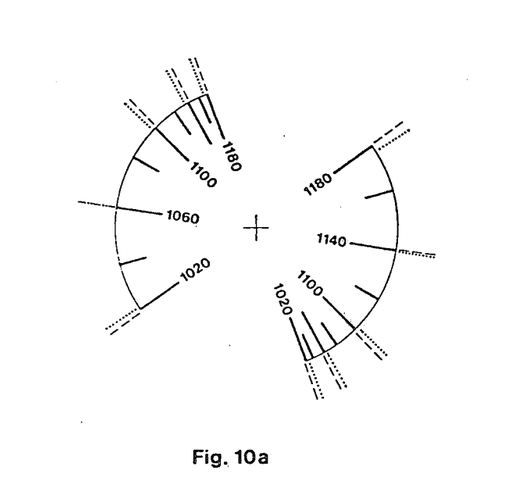
FIGS. 10a and 10b show a resultant temperature error in one form of the present invention.
Figure 10B:
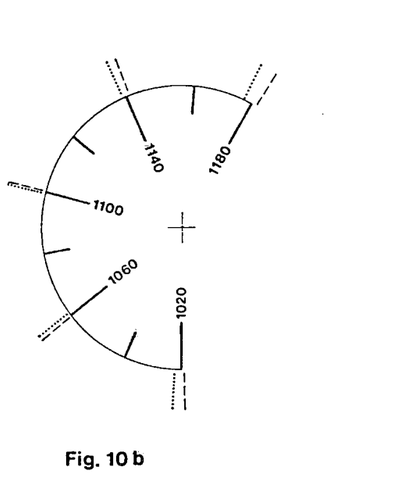

FIG. 10a shows the resultant temperature error for each float, whereas FIG. 10b shows the resultant temperature error on the density scale, this total error being the sum of the angular differences resulting from thermal expansion effects. Here again, the error at 0° C. is shown as a dashed line, and the error at +70° C. as a dotted line, and these are seen to be greatest at the extremes of the scale. In this case, however, the error of indicated density is less, being nowhere greater than +3 kg/m$^3$.

Figure 9:
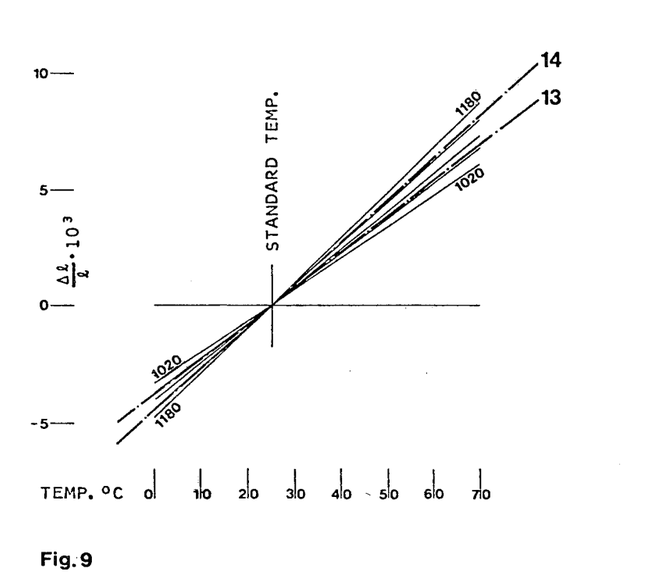
FIG. 9 is analogous to FIG. 7, but applicable to the present invention.

The summation of the temperature errors of the individual floats will be seen to follow a simple "rule of signs" which can be readily understood in connection with FIG. 9: If the thermal expansion of the fluid lies between the thermal expansions of the individual floats, the angular errors associated with the individual floats will have contrary signs, and the sum of the angular errors will be less than the greatest individual error; if the thermal expansion of the fluid is greater (or less) than the greatest (or least) thermal expansions of the individual floats, the individual errors will have like signs, and their sum will be greater than the greatest individual error. In the first case, a combination of float elements according to the invention will result in an absolute reduction of angular error due to thermal expansion, whereas in the second case the opposite will be true.

Figure 11:
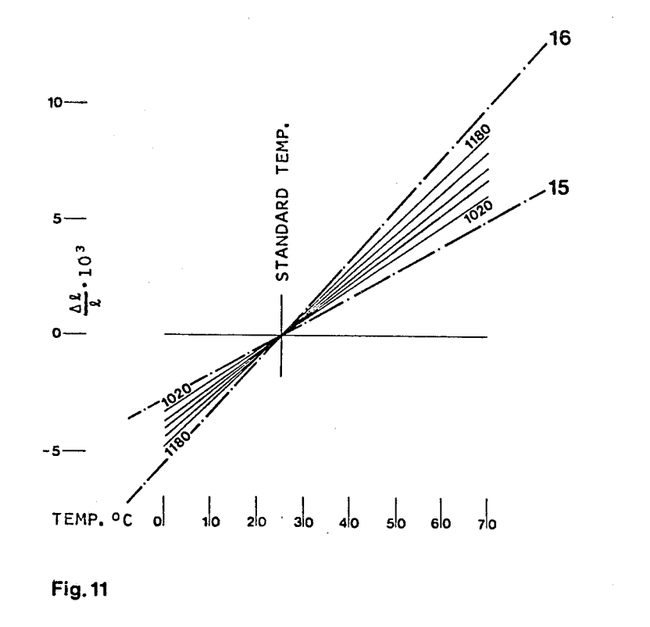
Figure 12:
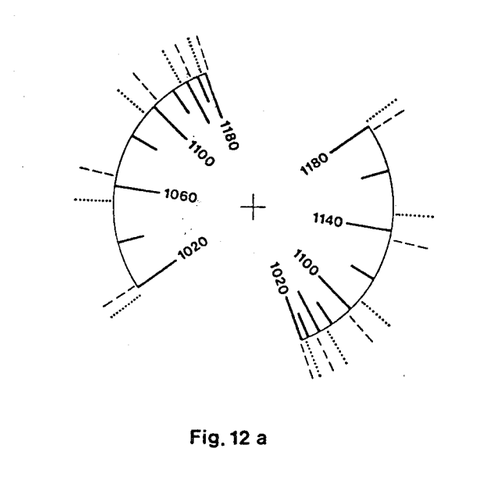
FIGS. 12a and 12b show the resultant temperature error in another form of the present invention.

In view of the above-mentioned "rule of signs", which is peculiar to the present invention, it is instructive to consider an example in which the total thermal-expansion range of the fluid lies between the thermal expansions of the individual floats, as shown in FIG. 11, where curve 15 represents the thermal expansion of float 1, and curve 16 the thermal expansion of float 2. In this case, the thermal expansion of the individual floats does not correspond to that of the fluid at any density, and FIG. 12a (which is analogous to FIG. 10a) shows that the angular differences corresponding to the temperature error of the individual floats are relatively large. In accordance with the "rule of signs", however, their summation as shown in FIG. 12b is much smaller than the individual errors, so that the errors of indicated density are nowhere greater than ±2.5 kg/m$^3$. Moreover, FIG. 12b shows full temperature compensation, not only at the midpoint of the scale, but now also near both extremes of the scale, where the individual angular differences are very nearly equal in value, but in contrary in sign.

The foregoing examples demonstrate the fact that in a device according to the present invention, bouyant materials having relatively wide-ranging coefficients of thermal expansion may be used, and yet the temperature compensation achieved by the device will be superior to what can be achieved with an ideal material in devices of previous type.

Figure 13:
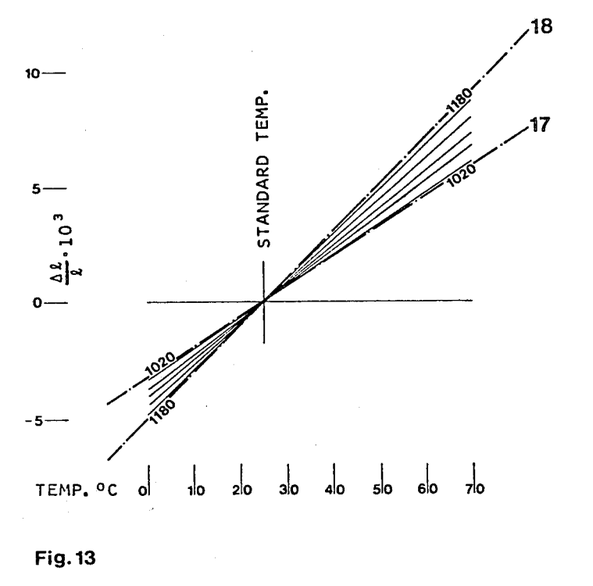
FIG. 13 shows a second alternative to FIG. 9.
Figure 14A:
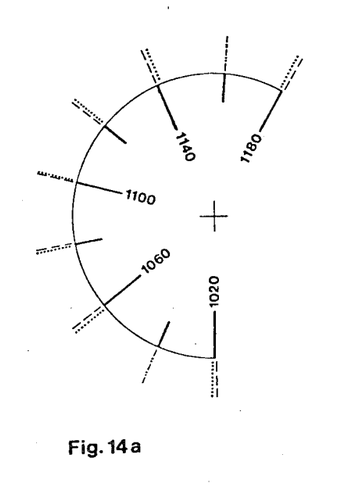
FIGS. 14a and 14b show a resultant temperature error in an ideal form of the present invention.

If, in the case of the present invention, ideal bouyant materials are assumed (analogous to the assumption of an ideal material for a conventional instrument as shown in FIGS. 7 and 8), the thermal expansion curves of floats 1 and 2 would appear approximately as shown by 17 and 18 in FIG. 13. FIG. 14a (which is analogous to FIGS. 10b and 12b) shows the total resultant temperature error, which is practically negligible, being nowhere greater than ±1 kg/m$^3$ over the temperature range from 0° C. to +70° C. Furthermore, it will be seen that temperature error is completely compensated at fluid densities near 1040, 1100, and 1160 kg/m$^3$. Because the total angular differences are so small, the actual values are presented in Table I, where $\Delta\alpha$ is the angular error of the individual float, $\Sigma\Delta\alpha$ is the summation of the angular errors of both floats at the stated temperature, and $\Sigma\Sigma\Delta\alpha$ is the total angular differences over the entire temperature range. Table I illustrates how the contrary signs of the individual angular errors $\Delta\alpha$ result in an absolute reduction of temperature error $\Sigma\Delta\alpha$ at all densities and temperatures.

TABLE I

| Standard fluid density | Temperature of density measurement | | | | | | |
|---|---|---|---|---|---|---|---|
| | 0° C. | | | +70° C. | | | |
| | float 1 $\Delta\alpha$ | float 2 $\Delta\alpha$ | $\Sigma\Delta\alpha$ | float 1 $\Delta\alpha$ | float 2 $\Delta\alpha$ | $\Sigma\Delta\alpha$ | $\Sigma\Sigma\Delta\alpha$ |
| 1020 | −0.7 | +0.1 | −0.6 | +1.3 | −0.2 | +1.1 | 1.7° |
| 1060 | −1.1 | +1.7 | +0.6 | +1.9 | −2.7 | −0.8 | 1.4° |
| 1100 | −1.7 | +1.6 | −0.1 | +3.0 | −2.8 | +0.2 | 0.3° |
| 1140 | −1.8 | +1.1 | −0.7 | +3.2 | −2.0 | +1.2 | 1.9° |
| 1180 | 0.0 | +0.8 | +0.8 | +0.2 | −1.5 | −1.3 | 2.1° |

Figure 14B:
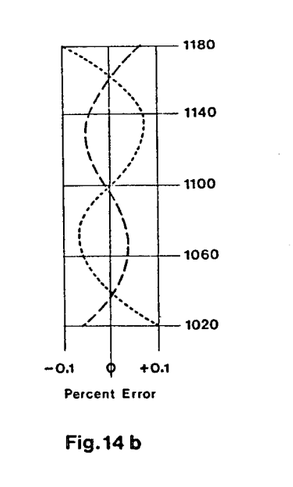

If the sum of the angular errors at each temperature extreme ($\Sigma\Delta\alpha$) is related to angular increments of density at the corresponding points of the scale, the maximum temperature error of the instrument can be expressed in percent of indicated density, which is more relevant than angular degrees. FIG. 14b shows this error graphically for the entire density range, the temperature error at 0° C. being shown as a dashed line and that at +70° C. as a dotted line. It is obvious that temperature compensation is greatly enhanced by the "S"-shaped error curves, which are peculiar to the present invention.

It was stated that the linearized thermal expansion curves used for the sake of simplicity in the foregoing comparative examples are idealized depictions of the properties of real materials. It should be pointed out that the validity of conclusions drawn from the examples is in no way dependent upon the linearity of thermal expansion curves as such, but rather upon the degree of divergence between curves pertaining to real fluids and curves pertaining to real float materials. In practice it will be found that the thermal expansion curves e.g., of a wide range of thermoplastics (which because of their density are well suited for use as a bouyant material) have characteristics similar to the thermal expansion curves of many aqueous solutions (e.g., battery acid, glycol anti-freeze, etc). In both cases, the curves are nonlinear, showing an increase in coefficients of thermal expansion with increasing temperature, and this agreement permits the designer to select a bouyant material that will provide adequate temperature compensation for a given fluid in a given range of densities and temperatures. It was stated that temperature compensation in devices of this type is achieved primarily through selection of a bouyant material with suitable thermal expansion; thus, in the present invention, the demands upon properties of materials are no more stringent than in devices of previous type. On the contrary, the foregoing examples of the invention, which assume three different pairs of bouyant materials (i.e., six different coefficients of thermal expansion), proved in every case to provide better temperature compensation than that achieved with an ideal material in a single-float instrument.

In order to exploit more fully the particular advantages of the present invention, it is a further purpose of the invention to provide new means of influencing the thermal expansion characteristics of the float elements. It was stated that in practice hitherto, metallic weight elements are used, and that their contribution to the thermal expansion characteristics of the float element as a whole is negligible. Contrary to this practice, it is within the scope of the present invention to utilize weight elements of relatively large volume and relatively large coefficients of thermal expansion, such that they contribute materially to the thermal expansion characteristics of the float element in such a way that these latter are no longer determined exclusively by the thermal expansion of the bouyant material. Obviously, such a weight element must satisfy the inequality $\rho_b > \rho$ for all values of $\rho$.

The extent to which such a weight element can modify the thermal expansion characteristics of the float element as a whole may be judged by evaluating the first term of equation (4). If the radii A and B are assumed to be equal, the term is reduced to $V_b/V_a$, and describes the relative volumes of the weight element and the bouyant element. In previous devices with metallic weight elements, this term would assume values—depending upon the given densities and associated float angles—ranging roughly from 0.015 to 0.04, i.e., the volume of the bouyant element would be 25 to 70 times greater than that of the weight element.

However, if the relative volumes are most nearly equal, the designer can utilize the thermal expansion of the weight element to modify the thermal expansion characteristics of the float element as a whole. This is accomplished in the present invention by using a weight element of relatively low density, such that the density of the weight element is not greater than four times the density of the bouyant element, i.e., $(\rho_b/\rho_a) < 4$. If, for example, the weight element is assumed to have a density about one and a half times greater than that of the bouyant element, the ratio $V_b/V_a$ would assume values ranging roughly from 0.3 to 3.0. Therefore, a weight element of specified density might have one third of the volume of the bouyant element, or it might have three times the volume of the bouyant element, depending upon the density range and associated angles assigned to the float element. Thus, the designer, having chosen two suitable materials, may further influence the relative volumes of the two materials, and thereby the thermal expansion characteristics of the float element as a whole, by varying the density range and/or the angular range of the float in question. From this it will be seen that the advantage resulting from the use of a low-density weight element according to the invention is not merely "additive", but rather provides a new dimension of design freedom, in which temperature compensation is no longer determined by the choice of materials alone.

As a further new means of influencing the thermal expansion characteristics of any float element, the present invention proposes a float assembly in which a difference between the coefficients of thermal expansion of the bouyant material and the weight material will result in a disproportional change in the hydrostatic radii of the respective elements with change in temperature. It was stated that in previous float elements the weight element is structurally incorporated into the bouyant element, so that the thermal expansion of the latter determines changes in the length of both radii, A and B, and that such changes are therefore proportional and without effect upon the thermal expansion characteristics of the float element. However, the utilization of relatively low-density (i.e., large-volume) weight elements as previously proposed in the invention makes it feasible to design float assemblies in which the relative angular positions of the bouyant element and weight element are maintained, while permitting different rates of change in the respective radii A and B, corresponding to the different expansion of the elements with change of temperature. In this case, the float angles will be governed by equation (5), rather than by equation (4) as heretofore.

Figure 15A:
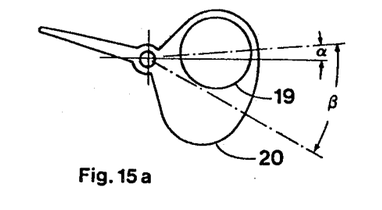
FIG. 15a shows an embodiment of a float element analogous to FIG. 6, but utilizing a low-density weight element.
Figure 15B:
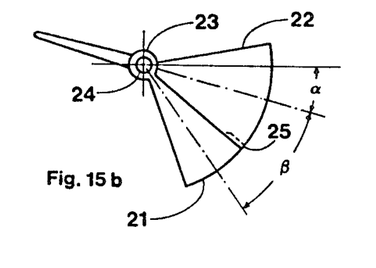
FIGS. 15b and 15c show embodiments of a float element analogous to FIG. 15a, but with modified ways of utilizing a low-density weight element.
Figure 15C:
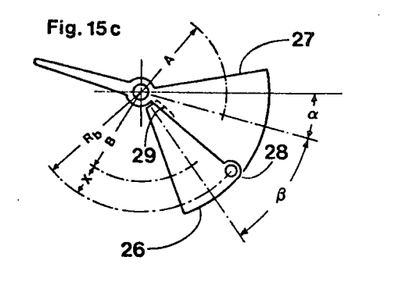

FIGS. 15a, b and c show embodiments of float elements utilizing the foregoing means to modify thermal expansion characteristics.

FIG. 15a shows an embodiment similar to index element 4 of FIG. 4, where the bouyant element 19 is structurally incorporated into a weight element 20 of relatively low density. This is a reversal of previous practice, and, since the thermal expansion of the weight element could be expected to be relatively small, the thermal expansion of the float element would be markedly less than that of the bouyant material alone. Here, the thermal expansion of the weight element governs the change in both radii, A and B, so that equation (4) still applies.

FIG. 15b shows a similar embodiment, where a relatively low-density weight element 21 and a bouyant element 22 have a fixed attachment at the pivotal point by means of concentric rings 23 and 24. A sliding "dovetail" attachment 25 prevents any angular displacement of the elements relative to each other, while permitting different radial expansions with change of temperature. If the two materials have different coefficients of thermal expansion, changes of temperature will cause disproportional changes of radii A and B, so that equation (5) applies. Since the fixed attachment of both elements is at the pivotal point, the attachment radius for both elements, $R_a$ and $R_b$, is zero, and the first term of equation (5) becomes:

$$\frac{V_b B \left(1 + \frac{\Delta b}{b}\right)}{V_a A \left(1 + \frac{\Delta a}{a}\right)}$$

FIG. 15c shows a similar embodiment, where the fixed attachment 28 of weight element 26 to bouyant element 27 is located at the periphery of the float, while a sliding attachment 29 prevents any relative angular displacement of the two elements. Here the bouyant element is likewise attached at the pivotal point, so that the radius of attachment $R_a$ is zero. The weight element, however, is attached at 28, so that its radius of attachment may be said to have a value B+X. Substitution in the first term of equation (5) gives:

$$\frac{V_b \left(B + (B + X)\frac{\Delta a}{a} - X\frac{\Delta b}{b}\right)}{V_a A \left(1 + \frac{\Delta a}{a}\right)}$$

Therefore, although the volumes and materials of the floats described in 15b and 15c might be identical, their thermal expansion characteristics would be different because of the structural modification of the respective attachment radii according to the invention.

Obviously, the foregoing principles may be applied to either or both of the float elements according to the present invention, and it has been said that their effects upon temperature compensation will depend upon the density range and corresponding angular range assigned to each float. Since a variety of suitable materials is available, and since the latter, as is well known, may be modified by the admixture of inert "fillers", it may be concluded that the particular advantages of the present invention can be fully exploited in practice.

By way of verifying the previously stated principles in applications with real materials, the case of a precision battery-acid tester may be considered as an example. The usual density range of such an instrument would be from 1100 to 1300 kg/m³, and the acid temperatures could be assumed to range from +10° C. to +45° C. In this example, the bouyant material of float 1 is assumed to be an unmodified high-density polyethylene, the bouyant material of float 2 an unmodified low-density polyethylene, and the weight material of both floats an unmodified polyfluorocarbon. The attachment radii of the float and weight elements are both zero, and the total scale angle is 210°, as in the previous examples.

Figure 16:
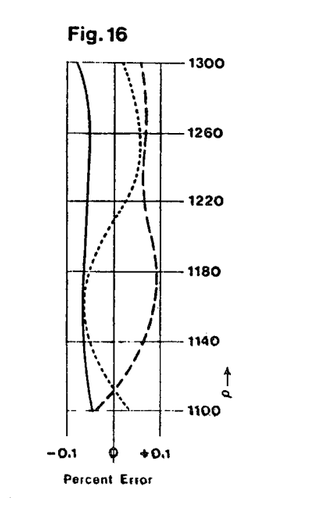
FIG. 16 shows a resultant temperature error in an application involving real materials.

FIG. 16 shows temperature error graphically in percent of indicated density at temperatures of +10° C. (dashed line), +25° C. (solid line), and +45° C. (dotted line). FIG. 16 fully confirms the conclusions drawn from the foregoing simplified assumptions, and demonstrates that by application of the principles of the present invention to real materials, temperature error can be reduced to an extent impossible with devices of prior type.

In this connection, it is important to consider the fact that, although the present device can be used simply by immersing it into a fluid the density of which is to be measured, more often such a device is made portable by enclosing it within a housing which is at least partly transparent, whereby some means (usually a compressible bulb) is provided for drawing a fluid sample into the housing in such a way that the float elements are immersed. In practice, it has been found that density measurements made with such portable devices are subject to serious errors, for the simple reason that the seemingly unavoidable air bubbles in the fluid sample tend to attach themselves to the float element, where their added bouyancy causes significant error in the float angle. It is necessary for the fluid inlet of such a housing to be small, since it is surface tension within this orifice which prevents involuntary outflow of the fluid sample once the inlet orifice is no longer immersed in the body of fluid from which the sample was drawn. Furthermore, a compressible bulb with sufficient elasticity to fill the housing within a reasonable time will cause a high pressure gradient at the inlet during the beginning of fluid inflow, when the bulb is most compressed. Also, at this time the weight of the fluid supported by the pressure gradient will be at a minimum. As a result, the inflow velocity will be high; flow speeds of 3 m/sec and more are not uncommon. In order to ensure that this jet of fluid will not impinge upon the elements contained within the housing, it is customary to provide the latter with interior deflectors of various forms. However, at such speeds the fluid jet disintegrates, regardless of where it impinges, and as a result the fluid sample will contain air bubbles, which may falsify the density measurement. For this reason, the user of such instruments is always instructed to tap them in order to remove air bubbles before taking a density reading.

This has been unavoidable, because a significant reduction of inflow speed—achieved, for example, by a reduction of bulb elasticity—would result in an intolerable prolongation of inflow time. The user of such an instrument would then tend to withdraw the inlet opening from the body of fluid from which the sample was being drawn before the bulb was fully expanded. In consequence, further expansion of the bulb would draw air bubbles into the housing at the end of fluid inflow, although such bubbles might have been avoided at the beginning.

Since this falsification of density measurements is a serious deficiency in devices of this type, it is a further purpose of the present invention to provide a means for preventing the formation of air bubbles in the fluid sample under normal conditions of use. To this end, the float elements as previously described are enclosed in a known housing which is at least partly transparent, and which is provided with a known means for drawing a fluid sample into the housing in such a manner that the float elements are immersed in the sample. The fluid inlet consists of a small exterior orifice which, according to the invention, is connected to the chamber containing the float elements by a channel of gradually increasing cross-section area, such that the area of cross-section at the point of entrance into the chamber is materially larger than the cross-section area of the exterior orifice. Since the quantity of fluid passing the exterior orifice at any given time must be equal to the quantity entering the housing chamber, the flow speed at these points will be inversely proportional to the area of cross-section.

The rate of deceleration within this channel will be limited by the fact that the resulting pressure gradient must be moderate if the fluid stream is not to become dissociated by the formation of air bubbles, which would be detrimental to the effect desired. Inflow speeds at the exterior orifice will of course vary with orifice size, and with the pressure gradient producing the inflow, but typical dimensions would result in Reynolds numbers not greater than $1 \cdot 10^4$. Under such conditions, it may be said that—depending upon the size of the exterior orifice and the arrangement of elements within the housing chamber—the largest cross-section area of the channel should be at least four times greater than that of the exterior orifice, and that a conical inlet should have a half-angle of not more than 5°.

However, a conical inlet channel of circular cross-section is not mandatory, and under certain circumstances it might be advantageous to utilize a divergent channel of rectangular or other cross-section form. In such cases, reference can be made to a criterion of similarity based on the circumference C and the area A of the channel cross-section. (This is analogous to the "hydraulic radius" A/C, which is a criterion of similarity for fluid flow in straight pipes). If dA is an increment of area corresponding to dL, an increment of length in the direction of flow, divergent channels may be considered similar if the expression $(1/C) \cdot (dA/dL)$ is similar. For a conical channel—in view of the small angles of divergence in question—this expression reduces to dr/dL, where r is the cross-section radius. The preceding specification can therefore be restated for a conical channel in the form:

$$0 < (dr/dL) < 0.09$$

and for any divergent channel according to the invention in the form:

$$0 < (1/C) \cdot (dA/dL) < 0.09$$

If the advantage resulting from utilization of a divergent inlet channel is to be retained under all practical conditions of use, it is necessary to consider the fact that in devices of this sort, the inlet is often provided with a tubular extension of some length suitable to a particular application. In such cases it is common practice to attach a length of flexible tubing which fits over the inlet orifice of the device. Since any significant length of tubing with very small diameter would increase inflow resistance and prolong inflow time, such tubing is almost always of materially larger inside diameter than the inlet orifice of the device itself.

Because of this, and because of uncontrolled movements of the flexible tubing, fluid contained in the tubing is often lost by involuntary outflow once the open end of the tubing is no longer immersed in the fluid from which the sample is being drawn. Although the amount of fluid thus lost is small, the height of the fluid column represented by the tubing is large compared with the height of the device as a whole. In consequence, the pressure equilibrium existing within the system at the end of fluid inflow is significantly disturbed by any loss of fluid from the tubing; the compressible bulb expands further and air is drawn into the device, even though there may be no loss of fluid through the inlet orifice itself. In the case of a very flexible compressive bulb, the slightest disturbance of pressure equilibrium can initiate bulb expansion, which in turn shortens the fluid column in the tubing, thus accelerating the process of aspiration whereby first fluid, then air, is drawn from the tubing into the housing chamber. This process may even assume an oscillatory character, whereby air intake alternates repeatedly with fluid loss.

Because of the importance of avoiding air bubbles and turbulence within the chamber containing the float elements, the invention provides further that the inlet channel be arranged in the form of an inverted "U"-tube, the highest point of which is located substantially higher than the point where the channel enters the housing chamber. By this means, air which passes the exterior orifice of the channel after the chamber is filled is entrapped at the highest point of the channel, whereby a hydrostatically stable condition is established, so that there is no air-bleed into, or loss of fluid from, the housing chamber itself.

Because the space available for accommodating the inlet channel as described would be limited in practice, it is preferable to provide a relatively greater degree of divergence in that part of the channel which is between the exterior orifice and the highest point, and a relatively lesser degree of divergence in that part of the channel which is between the highest point and the entrance of the channel into the housing chamber. By this feature, the negative acceleration of the fluid column which is induced by the divergence of the channel is greater where it is augmented by a negative gravitational acceleration, and relatively less where a positive gravitational acceleration, being contrary to that induced by the divergence of the channel, increases the risk of dissociation of the fluid column. By this means a maximum reduction of inflow speed may be achieved for any given channel length.

Figure 17:
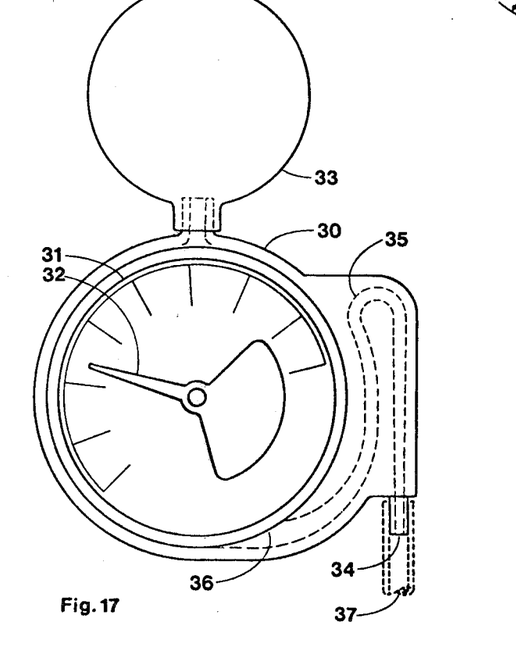
FIG. 17 shows a portable density measuring device.

FIG. 17 shows an example of a portable density-measuring device according to the invention. The transparent housing 30 contains the coaxially mounted pivoting float elements 31 and 32, and is fitted with a compressible bulb 33. The compressible volume of bulb 33 is such that the housing 30 can be completely filled with a fluid sample so that the float elements 31 and 32 are immersed in the latter. The fluid sample is admitted into the housing at the exterior orifice 34, from where it passes through channel 35 of gradually increasing cross-section area and enters the housing chamber at 36 with a materially reduced inflow speed. Channel 35 follows roughly the shape of an inverted "U"-tube, the highest point of which is located higher than point 36, where it enters the housing chamber. A suitable length of tubing 37 can be attached at exterior orifice 34.

I claim:

1. A device for measuring the density of a fluid having a density within a predetermined range, comprising a housing for containing the fluid, a first float element pivotal about a normally horizontal axis in said housing, a second float element pivotal about said axis, each of said elements including at least one buoyant volume that has a center of buoyancy displaced from said axis and a density which is less than the fluid density to be measured, and at least one weight volume that has its center of gravity displaced from said axis and a density greater than the fluid density to be measured, each of said elements being formed so that a radial line joining its center of buoyancy and said axis is angularly displaced from and above a radial line joining its center of gravity and said axis, and such that said elements rotate in opposite directions in response to buoyant forces, whereby because of differing buoyancy in fluids of different densities the relative angular positions of said elements about said axis indicate the density of the fluid in which they are immersed and said elements rotate in opposite directions about said axis with changes in the density of the fluids, said first float element comprising means for responding to equal increments of fluid density within said predetermined range with relatively larger angular increments of rotation about said axis in a lower section of said density range, said second float element comprising means for responding to equal increments of fluid density within said predetermined range with relatively larger angular increments of rotation about said axis in a higher section of said density range, so that the relative angular displacement of said elements in said lower section of said density range, is determined to a greater extent by said first element than by said second element and, in said higher section of said density range, to a greater extent by said second element than by said first element.

2. A device as claimed in claim 1, arranged to measure the density of a fluid having a density that within said range varies with the temperature of the fluid, and having thermal expansion characteristics that vary with density within said range, said first float element being formed so as to relatively approximate the thermal expansion of the fluid when the fluid is in a lower section of said range, and said second float element being formed so as to relatively approximate the thermal expansion of the fluid when the fluid is in a higher section of said range, whereby deviations in the angular positions about said axis of said first element due to temperature variations of the fluid are relatively small in said lower section of said density range, and deviations in the angular positions about said axis of said second element due to said temperature variations are relatively small in said higher section of said density range.

3. A device according to claim 2 wherein said float elements are formed from materials such that the difference between the average thermal expansion of the fluid and the thermal expansion of said first element is of approximately the same magnitude as, but opposite in sign to, the difference between the average thermal expansion of the fluid and the thermal expansion of said second element, whereby at any point in said density range deviations in the angular positions of said first element about said axis resulting from thermal expansion effects are of approximately the same magnitude as, but opposite in direction to, the corresponding deviations in the angular positions of said second element, the relative angular displacement of said elements about said axis resulting from thermal expansion effects thereby being of smaller magnitude than said deviations.

4. A device according to claim 1, arranged to measure the density of fluids having thermal expansion characteristics that vary with density within said range, said float elements being so formed that the thermal expansion of the fluids over said range lies between the thermal expansions of said float elements.

5. A device according to claim 1 wherein said housing is at least partially transparent and the device also includes suction means positioned for drawing a fluid sample into said housing so as completely to immerse said float elements, and duct means formed with a divergent channel for admitting said fluid sample into said housing, said channel having an inlet orifice located outside said housing at which the cross-sectional area of said divergent channel is smallest, and said channel so gradually increasing in cross-sectional area that the increment of cross-sectional area per increment of length at any point of said channel forms a ratio with the circumference at that point which is not greater than 0.09, the divergent length of said channel being such that the cross-sectional area increases at least by a factor of 4.

6. A device according to claim 5 wherein said divergent channel is formed as an inverted U-tube located with its highest point substantially higher than the point at which said channel enters said housing.

7. A device according to claim 6 wherein said channel has a relatively greater degree of divergence in that part of the channel which is between the exterior inlet orifice and the highest point, and a relatively lesser degree of divergence in that part of the channel which is between the highest point and the entrance of the channel into the housing chamber.

8. A device according to claim 1 wherein one of said float elements is marked with a scale corresponding to fluid density and the other of said float elements includes an index adjacent to said scale, said scale and said index being located to provide an indication of fluid density on said scale in all effective relative positions of said float elements within said predetermined density range.

9. A device for measuring the density of a fluid having a density within a predetermined range, comprising a housing for containing the fluid, a first float element pivotal about a normally horizontal axis in said housing, a second float element pivotal about said axis, each of said elements including at least one buoyant volume that has a center of buoyancy displaced from said axis, said buoyant volume having a density which is less than the fluid density to be measured, and at least one weight volume that has its center of gravity displaced from said axis and a density greater than the fluid density to be measured, each of said elements being formed so that a radial line joining said center of buoyancy and said axis is angularly displaced from and above a radial line joining said center of gravity and said axis, and such that said elements rotate in opposite directions in response to buoyant forces, whereby because of differing buoyancy in fluids of different densities the relative angular positions of said elements about said axis indicate the density of the fluid in which they are immersed and said elements rotate in opposite directions about said axis with changes in the density of the fluids, at least one of said float elements consisting of a relatively more dense weight volume and a relatively less dense buoyant volume, the density of said weight volume being less than four times the density of said buoyant volume whereby the size of said weight volume relative to said buoyant volume is such that the thermal expansion of said weight volume contributes materially to the thermal expansion of said float element.

10. A device for measuring the density of a fluid having a density within a predetermined range, comprising a housing for containing the fluid, a first float element pivotal about a normally horizontal axis in said housing, a second float element pivotal about said axis, each of said elements including at least one buoyant volume that has a center of buoyancy displaced from said axis, said buoyant volume having a density which is less than the fluid density to be measured, and at least one weight volume that has its center of gravity displaced from said axis and a density greater than the fluid density to be measured, each of said elements being formed so that a radial line joining said center of buoyancy and said axis is angularly displaced from and above a radial line joining said center of gravity and said axis, and such that said elements rotate in opposite directions in response to buoyant forces, whereby because of differing buoyancy in fluids of different densities the relative angular positions of said elements about said axis indicate the density of the fluid in which they are immersed and said elements rotate in opposite directions about said axis with changes in the density of the fluids, at least one of said float elements consisting of a buoyant volume having a center of buoyancy and a weight volume having a center of gravity which is angularly displaced from said center of buoyancy, said volumes having a common pivotal point concentric to said axis and being constrained against relative angular displacement of said centers but unconstrained against individual radial thermal expansion with respect to said axis, such that said angular displacement of said centers is maintained when said volumes undergo individual radial thermal expansion with respect to said axis resulting in a mutually independent radial displacement of said center of buoyancy relative to said center of gravity which is governed solely by the individual coefficients of thermal expansion of said volumes.

11. A device for measuring the density of a fluid having a density within a predetermined range, comprising a housing for containing the fluid, a first float element pivotal about a normally horizontal axis in said housing, a second float element pivotal about said axis, each of said elements including at least one buoyant volume that has a center of buoyancy displaced from said axis, said buoyant volume having a density which is less than the fluid density to be measured, and at least one weight volume that has its center of gravity displaced from said axis and a density greater than the fluid density to be measured, each of said elements being formed so that a radial line joining said center of buoyancy and said axis is angularly displaced from and above a radial line joining said center of gravity and said axis, and such that said elements rotate in opposite directions in response to buoyant forces, whereby because of differing buoyancy in fluids of differing densities the relative angular positions of said elements about said axis indicate the density of the fluid in which they are immersed and said elements rotate in opposite directions about said axis with changes in the density of the fluids, at least one of said float elements consisting of a buoyant volume having a center of buoyancy and a weight volume having a center of gravity which is angularly displaced from said center of buoyancy, one of said volumes being attached pivotally to said axis and the other of said volumes being attached to said one of said volumes at a point radially distant from said axis for individual radial thermal expansion relative to said one of said volumes, said other volume being thereby attached indirectly to said axis and arranged for said angular displacement of said centers to be maintained, whereby changes of temperature affecting said volumes result in radial displacement of said center of said indirectly attached volume governed by the coefficient of thermal expansion of said pivotally attached volume and by the coefficient of thermal expansion of said indirectly attached volume affecting the radial displacement of said center of said indirectly attached volume relative to said pivotally attached volume.

* * * * *